United States Patent [19]
MacDonald et al.

[11] Patent Number: 5,269,321
[45] Date of Patent: Dec. 14, 1993

[54] RETRIEVABLE PESSARY

[75] Inventors: Ishbel A. MacDonald, Glasgow;
Andrew G. Muddle, Strathaven;
Lindesay R. MacFarlane, Glasgow,
all of Scotland

[73] Assignee: Controlled Therapeutics (Scotland) Ltd., Glasgow, Scotland

[21] Appl. No.: 913,245

[22] Filed: Jul. 14, 1992

[51] Int. Cl.$^5$ ............................................... A61F 6/06
[52] U.S. Cl. ................................... 128/830; 128/834
[58] Field of Search ................... 128/830, 841; 604/2, 604/358, 364, 368, 371, 378

[56] References Cited

U.S. PATENT DOCUMENTS

| | | | |
|---|---|---|---|
| 2,687,729 | 8/1954 | Slavin | 128/270 |
| 3,261,353 | 7/1966 | Johnson | 128/832 |
| 3,545,439 | 12/1970 | Duncan | 128/832 |
| 3,780,730 | 12/1973 | Weisman | 128/832 |
| 3,815,601 | 6/1974 | Schaefer | 13/20 |
| 3,975,350 | 8/1976 | Hudgin | 128/832 |
| 4,014,987 | 3/1977 | Heller | 128/832 |
| 4,034,756 | 7/1977 | Higuchi | 128/832 |
| 4,198,976 | 4/1980 | Drobish | 128/832 |

FOREIGN PATENT DOCUMENTS

| | | |
|---|---|---|
| 9200756.1 | 4/1992 | Fed. Rep. of Germany . |
| 860975 | 1/1941 | France . |
| 2463609 | 2/1981 | France . |
| WO81/00093 | 8/1982 | PCT Int'l Appl. . |
| WO84/04666 | 12/1984 | PCT Int'l Appl. . |
| 292745 | 6/1928 | United Kingdom . |
| 606527 | 10/1945 | United Kingdom . |
| 620586 | 3/1946 | United Kingdom . |
| 2025231A | 1/1980 | United Kingdom . |
| 2047093 | 11/1980 | United Kingdom . |
| 2200285A | 8/1988 | United Kingdom . |

OTHER PUBLICATIONS

John Hopkins Protocol, dated Nov. 1990–Jan. 1991.
John Hopkins Statement of Investigator, dated Nov. 20, 1990.
University of Tennessee Clinical Study Acceptance, dated Dec. 19, 1990.
University of Tennessee Protocol, dated Jan. 14, 1991.
University of Tennessee Research Agreement, dated Feb. 11, 1991.
University of Tennessee Informed Consent Forms, various dates 1990–1991.
University of Tennessee Case Report Forms, dated Feb. 14, 1991.
UK–Plymouth General Hospital Protocol, dated Mar. 12, 1992.
UK–Plymouth General Hospital Case Report Forms, dated May 11, 1992.
UK–Plymouth General Hospital Informed Consent Forms, various dates 1992.

*Primary Examiner*—Michael A. Brown
*Attorney, Agent, or Firm*—Gunn, Lee & Miller

[57] ABSTRACT

A retrievable pessary for intravaginal or intrarectal use comprises a solid body comprising a pharmaceutically active ingredient; a net pouch which encloses the body; and a withdrawal cord attached to the pouch to enable the pessary to be withdrawn after use.

3 Claims, 2 Drawing Sheets

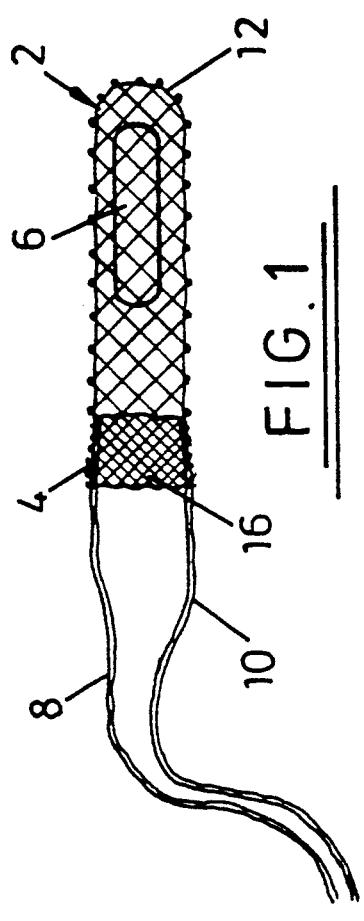
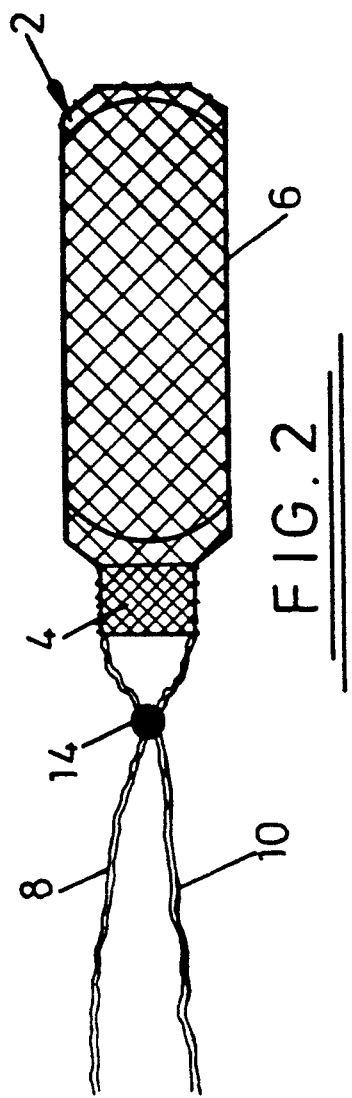

RETRIEVABLE PESSARY

BACKGROUND OF THE INVENTION

FIELD OF THE INVENTION

The present invention relates to a retrievable pessary for intravaginal or intrarectal use, which may be inserted and retrieved again once the pharmacologically active ingredient contained therein has been substantially released.

DESCRIPTION OF RELATED ART

Controlled release pessaries are already known and typically comprise a solid polymer body containing a pharmacologically active substance, which is released in a controlled release or sustained release manner so as to provide a controlled dosage of the active substance over a prolonged time period. One such pessary sold for intravaginal use under the trademark PROPESS contained a prostaglandin. Prostaglandins play an important role in the gravid uterus, at or near term in pregnancy. They induce structural changes in cervical smooth muscle fibers, resulting in softening and changes in shape that produce a ripening of the cervix. A sustained release of the prostaglandin is required over a time period or several hours just prior to birth. However, whilst these pessaries can be inserted relatively simply by the obstetrician, their removal may pose problems since it may be difficult to find and grip the pessary again.

Intravaginal articles, such as tampons, which have strings to allow removal of the device are already known. Tampon constructions are known from patent specifications GB 606527, GB 620586, GB 2025231, GB 2200285, and U.S. Pat. No. 3,815,601. Generally speaking, these comprise absorbent bodies designed to absorb body fluids and are provided with a string for retrieval purposes. They do not include active agents. The strings are usually attached directly to the device itself. Unfortunately, this is not necessarily appropriate for controlled release devices with which the present invention is concerned, since the solid polymer body containing the pharmacologically active ingredient often lacks the necessary physical strength or integrity to provide a satisfactory anchoring point for the removal string.

Intrauterine contraceptive devices are also known and are disclosed, for example in patent specification WO 82/02489. These may comprise an active ingredient such as a spermicide (which is non-systemic), but it is practically speaking not possible to include any retrieval cord since this would obstruct sexual intercourse.

SUMMARY OF THE INVENTION

It is an object of the present invention to mitigate the problems mentioned above, and to provide a pessary which is more easily and reliably retrievable.

Generally speaking, the present invention involves using a net having sufficient strength to attach retrieval means thereto.

In particular, the present invention provides a retrievable pessary for intravaginal or intrarectal use which comprises;
  a solid body comprising a pharmacologically active ingredient adapted to be released in a controlled manner from the body;
  net retaining means formed of a biologically acceptable material and engaging the solid body; and
  elongate retrieval means attached at one end thereof to the net retaining means to enable the pessary to be withdrawn from the vagina or rectal cavity after use.

The nature of the solid body is not of primary importance but the invention is particularly applicable to bodies having insufficient strength to retain normal retrieval means. The solid body is usually a polymer but might be any other type of controlled release structure such as a leachable-glass.

Generally the solid polymer body is non-biodegradable (in contrast to certain biodegradable or erodible controlled release systems known in the art) such that the solid body is not dispersed inside the patient but requires to be removed after release of the pharmacologically active ingredient to the extent desired. Many such non-biodegradable solid polymer bodies are known in the art and typically comprise water-swellable polymers capable of absorbing substantial amounts of aqueous liquid to increase their size several fold. For example, controlled release polymers based on cross-linked polyethylene glycol are capable of swelling to 1.2 to 5, particularly 1.5 to 3 times (on a weight basis) the original unswollen state. Such swellable hydrogels are typically described in patent specifications GB 2047093 and GB 2047094.

The period of time over which the controlled release of pharmacologically active ingredient is to take place will vary according to the nature of the ingredient and the pharmacologically effect to be achieved. In the case of prostaglandins, release is usually required over a relatively short time period, for example 1 to 10 hours. However, the retrievable pessary of the present invention has more general utility for the administration of drugs into the body which may be absorbed through the vaginal or rectal wall into the patient's system. In such cases, controlled release may be arranged to occur over days, weeks or even months according to the nature of the active ingredient and the desired pharmacological effect. Release of the active ingredient may be controlled by diffusion through the solid polymer body to its outer surface, or may be controlled by solubility of the active ingredient in the surrounding body fluid, depending on the nature of the active ingredient itself. The rate of release usually depends on a variety of factors, such as the shape, thickness and degree of cross-linking of the solid polymer body, the nature of the active ingredient and the nature of the polymer itself.

The administered dose may be controlled by removing the pessary prior to exhaustion of the active ingredient, for example when the appropriate pharmacological response has been delivered.

The net retaining means is formed of a biologically-acceptable perforate material, such as a net (including knitted, woven and non-woven materials, synthetic nets and expanded porous films).

Where the polymer swells in use, a pouch should be arranged such that whilst conforming to the initial size of the polymer body, is capable of stretching as the polymer swells. Knitted structures are particularly useful for this. Alternatively, the material from which the pouch is made may itself have the desired stretchability or elasticity.

It is particularly preferred that the pouch be produced in a seamless manner e.g. by circular knitting, so as to minimize seams or other protrusions which might lead to irritation within the patient. The pouch will usually have a slit, slot or other aperture for insertion of the solid polymer body.

Usually, the total length of the retrievable pessary is 25-35 cm. The pouch is generally of length 1 to 15 cm (preferably 5 to 15 cm for a suppository and 4 to 10 cm for a vaginal pessary) and of width 0.3 to 1 cm.

In one embodiment of the invention, the elongate retrieval means are integrally formed with the pouch, for example by knitting a continuous tape including a pouch portion into which the polymer body is inserted. Alternatively, a continuous knitted tube could be employed which is sealed at one end (using ultrasonics or heat) before inserting the solid body and sealing across the tube to create a pouch around the body, and to leave a long free end (which may in turn be sealed) as retrieval means.

In a second embodiment, the elongate retrieval means is separate from the pouch (and is typically in the form of a cord of the type used for withdrawal of tampons) which is integrated into the structure of the pouch during formation thereof. Preferably, the retrieval cord has two long ends and a central section passing down either side of the pouch from its open end and around its closed end. A neck piece may also be provided around the open end of the pouch. This prevents ripping and fraying of the net, and helps prevent accidental removal of the pessary.

The elongate retrieval means are formed of a biologically-acceptable material, typically a synthetic or natural polymer such as a polyester optionally including cotton.

BRIEF DESCRIPTION OF THE DRAWINGS

Embodiments of the present invention will now be described by way of example only with reference to the drawings which are to some extent schematic, wherein:

FIG. 1 is a side view of a first embodiment in its initial state;

FIG. 2 is a view of the pessary in a swollen state;

DETAILED DESCRIPTION OF THE PREFERRED EMBODIMENTS

Figure 3:
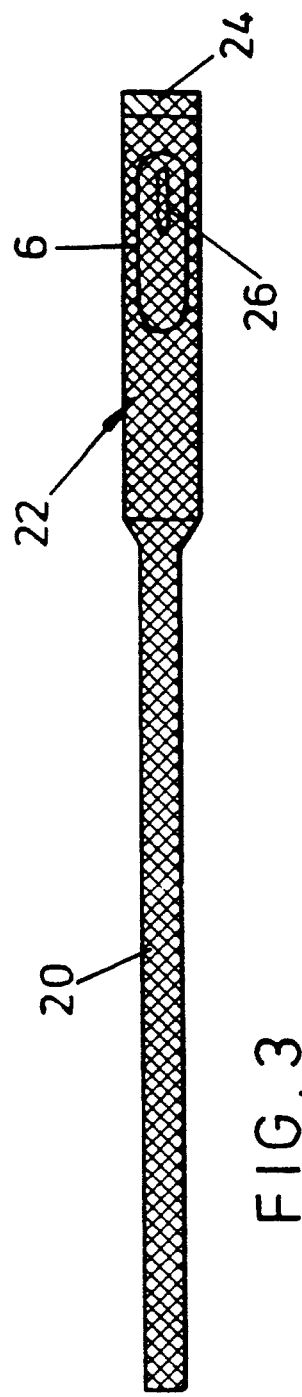
FIG. 3 is a view of a second embodiment having an integrally formed retrieval tape.

The embodiments shown in FIGS. 1 and 2 comprises a pouch 2 having a neck 4 and enclosing a controlled release swellable polymer body 6, a withdrawal cord having end portions 8, 10 and a central portion 12 is provided for retrieving the pessary.

The lozenge shaped polymer body 56 has a dry (and wet) length substantially 30 mm (48 mm), width substantially 9 mm (15 mm) and thickness 0.8 to 1.1 mm (1.9 mm) and is formed of a cross-linked polyethylene glycol. On swelling in contact with body fluids, it is capable of expansion of approximately 325% (i.e. takes up 325% by weight of water). The polymer allows for diffusion control release of a pharmacologically active ingredient (for example prostaglandin $PGE_2$) though many other applicable active ingredient will be known to the skilled man and the present invention is not limited to any particular one of these.

The pouch (2) is netted and formed of a texturized Dacron or Diolen polymer yarn of a single feed knitted construction formed on a Lilliput knitting machine. The seamless pouch is produced by circular knitting. The knitted construction imparts extensive elasticity to the pouch, which closely conforms to the shape of the polymer body (6) both in the initial and swollen states. The pouch is closed at one end and has an open end (16) through which the polymer body is introduced during assembly. The mouth area is strengthened by means of a neck piece (4) knitted from the same polyester yarn in a denser construction.

The retrieval cord comprises long end portions (8), (10) and a central portion (12) which extends down opposed sides of the pouch and around its closed end. The cord is sewn into the pouch during formation thereof so as to avoid the use of seams or adhesives.

the cord is sewn into the pouch by making the cord one of the two threads fed to a sewing machine. The cord is sewn down one side and around the end of a tube of the netted material (thereby closing the end), and back up the other side. The pouch is trimmed to shape, before being turned inside out so that the cord runs around the inside of the pouch.

Once the polymer body (6) has been introduced into the net pouch 2, the open end 16 may be closed by means of a knot 14 in the retrieval cord. The free ends of the cord may also be knotted (not shown) or one of the strings can be cut short, so as to effectively leave a single retrieval cord.

The pessary is introduced in its non-swollen state into the patient leaving the retrieval cord hanging out. When retrieval is required, this is simply a matter of gentle pulling on the free ends of the retrieval cord so as to withdraw the swollen pessary.

Figure 4:
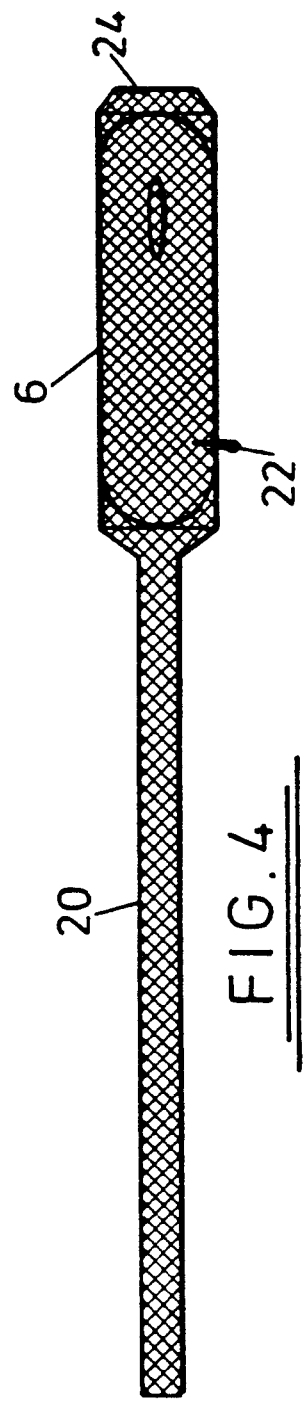
FIG. 4 shows a second embodiment in its swollen state.

FIGS. 3 and 4 show a second embodiment wherein the retrieval means is an integrally formed elongate tape (20). The tape is integrally formed on a double bed Rachelle frame from a texturized Dacron polyester yarn and comprises a pouch portion (22) and a closed end portion (24). A longitudinally extending slot (26) is provided for introducing the polymer body (6). Alternatively, the slot could extend transversely or at an angle to the longitudinal direction. Preferably the slot is adjacent to the closed end (24) of the pouch, but could in principal be anywhere on the pouch provided that the polymer body is effectively retained. The slot is located such that the end of the polymer body cannot inadvertently find its way into the slot, leading to loss of the body from the pouch. The tape, pouch, closed end and slot may be integrally formed on the knitting machine by appropriate programming thereof. The pouch portion (22) is arranged to be stretchable so as to substantially conform to the shape of the polymer body in both its initial and swollen states.

Insertion into a patient is carried out as before by a medical practitioner, and the device may be retrieved after use by means of the withdrawal tape.

Equally, the above-described embodiments could be adapted to take a suppository by minor adjustment of dimensions. A typical suppository is cylindrical with a rounded end and has dry (and wet) dimensions length 40 mm (60 mm) diameter 10 mm (16 mm); and a selling of approximately 220%.

We claim:

1. A retrievable pessary for intravaginal or intrarectal use which comprises:
   an elongate solid body formed of a water-swellable hydrogel and comprising a pharmacologically active ingredient adapted to be released in a controlled manner from said solid body, said solid body being non-biodegradable and non-erodible such that said solid body is not dispersed inside the patient during use; and a net retaining means formed of a biologically acceptable material, said net retaining means integrally formed by knitting, said net retaining means comprising:

a longitudinally extending knitted pouch portion enclosing said solid body, said knitted pouch portion being stretchable so as to accommodate swelling of said water-swellable hydrogel body during use from an initial state to a swollen state, said knitted pouch portion having a first end and a second end opposite said first end, said second end being closed; and an elongate extension integrally formed with said knitted pouch portion and extending from said first end of said pouch portion, said extension constituting an elongate retrieval means to enable said pessary to be withdrawn from the vagina or rectal cavity after use, said elongate retrieval means being in the form of a tape;

said knitted pouch portion having a slot in a wall thereof, said slot allowing insertion of said solid body into said pouch portion, said slot extending longitudinally along said pouch portion, said slot located adjacent to said second closed end of said pouch portion such that said solid water-swellable hydrogel body is retained in said pouch portion as said solid body swells from said initial state to said swollen state.

2. The pessary according to claim 1 wherein said pharmacologically active ingredient is capable of being systemically absorbed into the patient.

3. The pessary according to claim 1 wherein said elongate solid body is lozenge shaped.

* * * * *